United States Patent [19]

Coen et al.

[11] Patent Number: 5,223,391

[45] Date of Patent: Jun. 29, 1993

[54] INHIBITORS OF HERPES SIMPLEX VIRUS REPLICATION

[75] Inventors: Donald M. Coen, Medfield; Paul E. Digard, Brookline, both of Mass.

[73] Assignee: President and Fellows of Harvard College, Cambridge, Mass.

[21] Appl. No.: 482,634

[22] Filed: Feb. 21, 1990

[51] Int. Cl.$^5$ .............................................. C12Q 1/70
[52] U.S. Cl. .......................................... 435/5; 435/6; 435/7.21; 435/7.4
[58] Field of Search ....................... 435/5, 6, 7.1, 7.21, 435/7.4, 235.1

[56] References Cited

PUBLICATIONS

Gallo et al., "Purification of the Herpes Simplex Virus Type 1 65-Kilodalton DNA-Binding Protein: Properties of the Protein, etc.", J. Virol. 62:8 (1988).

Quinn et al., "DNA Sequence of the Region in the Genome of Herpes Simplex Virus Type 1 Containing the Genes for DNA Polymerase and the Major DNA Binding Protein", Nucleic Acids Res. 13:8143 (1985).

Powell et al., "Nonstructural Proteins of Herpes Simplex Virus/Purification of the Induced DNA Polymerase", J. Virol. 24:618 (1977).

Gallo et al., "The Essential 65-Kilodalton DNA-Binding Protein of Herpes Simplex Virus Stimulates the Virus Encoded DNA Polymerase", J. Virol. 63:5023 (1989).

Meek et al., "Inhibition of HIV-1 Protease in Infected T-Lymphocytes by Synthetic Peptide Analogues", Nature 343:90 (1990).

Laemmli, "Cleavage of Structural Proteins During the Assembly of the Head of Bacteriophage T-4", Nature 227:680 (1970).

Olivo et al., "Herpes Simplex Virus Type 1 Gene Products Required for DNA Replication: Identification and Overexpression", J. of Virol. 63:196 (1989).

McKnight et al., "Transcriptional Control Signals of a Eukaryotic Protein-Coding Gene", Science 217:316 (1982).

Taylor et al., "The Rapid Generation of Oligonucleotide-Directed Mutations at High Frequency Using Phosphorothioate-Modified DNA", Nucleic Acids Res. 13:8765 (1985).

Melton et al., "Efficient in Vitro Synthesis of Biologically Active RNA and RNA Hybridization Probes from Plasmids Containing a Bacteriophage SP6 Promoter", Nucleic Acids Res. 12:7035 (1984).

Krieg et al., "Functional Messenger RNAs are Produced by SP6 in Vitro Transcription of Cloned cDNAs", Nucleic Acids Research 12:7057 (1984).

Green et al., "Autonomous Functional Domains of Chemically Synthesized Human Immunodeficiency Virus TAT Trans-Activator Protein", Cell 55:1179 (1988).

Frankel et al., "Cellular Uptake of the TAT Protein from Human Immunodeficiency Virus", Cell 55:1189 (1988).

McGeoch et al., "The Complete DNA Sequence of the Long Unique Region in the Genome of Herpes Simplex Virus Type 1", J. Gen. Virol. 69:1531 (1988).

Fechheimer et al., "Transfection of Mammalian Cells with Plasmid DNA by Scrape Loading and Sonication Loading", Proc. Nat. Aca. Sci. 84:8463 (1987).

Dreyer et al., "Inhibition of Human Immunodeficiency Virus 1 Protease in Vitro: Rational Design of Substrate Analogue Inhibitors", Proc. Nat. Aca. Sci. 86:9752 (1989).

Yager et al., "Analysis of the Transcript of the Herpes Simplex Virus DNA Polymerase Gene Provides Evidence", etc., J. Virol 62:2007 (1988).

Elias et al., "A DNA Binding Protein Specific for an Origin of Replication of Herpes Simplex Virus Type 1", Proc. Nat. Aca. Sci. 83:6322 (1986).

(List continued on next page.)

Primary Examiner—David Saunders
Assistant Examiner—Donna C. Wortman

[57] ABSTRACT

An immunoassay for identifying an inhibitor of HSV DNA replication including providing a DNA polymerizing complex that includes two complex members, the complex members being HSV DNA polymerase and UL42, providing a potential inhibitor that inhibits the binding of HSV DNA polymerase to UL42, mixing the complex members in the presence of the potential inhibitor, and determining whether the potential inhibitor inhibits formation of the complex.

18 Claims, 16 Drawing Sheets

OTHER PUBLICATIONS

Wu et al., "Identification of Herpes Simplex Virus Type 1 Genes Required for Origin-Dependent DNA Synthesis", J. Virol. 62:435 (1988).

Lobel et al., "Construction of Mutants of Moloney Murine Leukemia Virus by Suppressor-Linker Insertional Mutagensis: Positions of Viable Insertion Mutations", Proc. Nat. Aca. Sci. 81:4149 (1984).

De Luca et al., "Isolation and Characterization of Deletion Mutants of Herpes Simplex Virus Type 1 in the Gene, etc.", J. of Virol. 56:558 (1985).

Gibbs et al., "Sequence and Mapping Analyses of the Herpes Simplex Virus DNA Polymerase Gene Predict A C-Terminal Substrate Binding Domain", Proc. Natl. Acad. Sci USA 82:7969 (1985).

Dutia et al., "Specific Inhibition of Herpesvirus Ribonucleotide Reductase by Synthetic Peptides", Nature 321:439 (1986).

Kotler et al., "Synthetic Peptides as Substrates and Inhibitors of a Retroviral Protease", Proc. Natl. Acad. Sci USA 85:4185 (1988).

McQuade et al., "A Synthetic HIV-1 Protease Inhibitor with Antiviral Activity Arrests HIV-Like Particle Maturation", Science 247:454 (1990).

Friedman et al., "Expression of a Truncated Viral Trans-Activator Selectively Impedes Lytic Infection by its Cognate Virus", Nature 335:452 (1988).

Green et al., "Mutational Analysis of HIV-1 TAT Minimal Domain Peptides:Identification of Transdominant Mutants that Suppress HIV-LTR-Driven Gene Expression", Cell 58:215 (1989).

Cohen et al., "Speicific Inhibition of Herpesvirus Ribonucleotide Reductase by a Nonapeptide Derived from the Carboxy Terminus of Subunit 2", Nature 321:441-443 (1986).

McClements et al., "Oligopeptides Inhibit the Ribonucleotide Reductase of Herpes Simplex Virus by Causing Subunit Separation", Virol. 162:270-273 (Jan. 1988).

L. D. Goodrich et al., Journal of Virology, vol. 63, 1989, pp. 137-147.

R. Heilbronn et al., Journal of Virology, vol. 63, 1989, pp. 3683-3692.

J. J. Crute et al., The Journal of Biology Chemistry, vol 264, 1989, pp. 19266-19270.

| | |
|---|---|
| TATATTATTA GCACAAAGTG CGAACGCTTC GCGTTCTCAC TTTTTTTATA ATAGCCGCCA | 60 |
| CGCCCACCCG CTACGTCACG CTCCTGTCGG CCGCCGGCCG TCCATAAGCC CGGCCGGCCG | 120 |
| GGCCGACGCG AATAAACCGG GCCGCCGGCC GGGGCGCCGC GCAGCAGCTC GCCGCCCGGA | 180 |

```
TCCGCCAGAC AAACAAGGCC CTTGCAC ATG CCG GCC CGG GCG AGC CTG GGG GTC   234
                            Met Pro Ala Arg Ala Ser Leu Gly Val

CGG TAA                                                              240
Arg End

TTTTGCCATC CCACCCAAGC GGCTTTTGGG GTTTTTCCTC TTCCCCCCTC CCCACATCCC   300

CCCTCTTTAG GGGTTCGGGT GGGAACAACC GCG ATG TTT TCC GGT GGC GGC CCG   354
                                    Met Phe Ser Gly Gly Gly Pro

CTG TCC CCC GGA GGA AAG TCG GCG GCC AGG GCG GCG TCC GGG TTT TTT   402
Leu Ser Pro Gly Gly Lys Ser Ala Ala Arg Ala Ala Ser Gly Phe Phe

GCG CCC GCC GGC CCT CGC GGA GCC GGC CGG GGA CCC CCG CCT TGT TTG   450
Ala Pro Ala Gly Pro Arg Gly Ala Gly Arg Gly Pro Pro Pro Cys Leu

AGG CAA AAC TTT TAC AAC CCC TAC CTC GCC CCA GTC GGG ACG CAA CAG   498
Arg Gln Asn Phe Tyr Asn Pro Tyr Leu Ala Pro Val Gly Thr Gln Gln
```

FIG. 1a

```
AAG CCG ACC GGG CCA ACC CAG CGC CAT ACG TAC TAT AGC GAA TGC GAT    546
Lys Pro Thr Gly Pro Thr Gln Arg His Thr Tyr Tyr Ser Glu Cys Asp

GAA TTT CGA TTC ATC GCC CCG CGG GTG CTG GAC GAG CAT GCC CCC CCG    594
Glu Phe Arg Phe Ile Ala Pro Arg Val Leu Asp Glu Asp Ala Pro Pro

GAG AAG CGC GCC GGG GTG CAC GAC GGT CAC CTC AAG CGC GCC CCC AAG    642
Glu Lys Arg Ala Gly Val His Asp Gly His Leu Lys Arg Ala Pro Lys

GTG TAC TGC GGG GGG GAC GAG CGC GAC GTC CTC CGC GTC GGG TCG GGC    690
Val Tyr Cys Gly Gly Asp Glu Arg Asp Val Leu Arg Val Gly Ser Gly

GGC TTC TGG CCG CGG CGC TCG CGC CTG TGG GGC GGC GTG GAC CAC GCC    738
Gly Phe Trp Pro Arg Arg Ser Arg Leu Trp Gly Gly Val Asp His Ala

CCG GCG GGG TTC AAC CCC ACC GTC ACC GTC TTT CAC GTG TAC GAC ATC    786
Pro Ala Gly Phe Asn Pro Thr Val Thr Val Phe His Val Tyr Asp Ile

CTG GAG AAC GTG GAG CAC GCG TAC GGC ATG CGC GCG GCC CAG TTC CAC    834
Leu Glu Asn Val Glu His Ala Tyr Gly Met Arg Ala Ala Gln Phe His

GCG CGG TTT ATG GAC GCC ATC ACA CCG ACG GGG ACC GTC ATC ACG CTC    882
Ala Arg Phe Met Asp Ala Ile Thr Pro Thr Gly Thr Val Ile Thr Leu
```

FIG. 1b

```
CTG GGC CTG ACT CCG GAA GGC CAC CGG GTG GCC GTT CAC GTT TAC GGC  930
Leu Gly Leu Thr Pro Glu Gly His Arg Val Ala Val His Val Tyr Gly

ACG CGG CAG TAC TTT TAC ATG AAC AAG GAG GAG GTT GAC AGG CAC CTA  978
Thr Arg Gln Tyr Phe Tyr Met Asn Lys Glu Glu Val Asp Arg His Leu

CAA TGC CGC GCC CCA CGA GAT CTC TGC GAG CGC ATG GCC GCG GCC CTG  1026
Gln Cys Arg Ala Pro Arg Asp Leu Cys Glu Arg Met Ala Ala Ala Leu

CGC GAG TCC CCG GGC GCG TCG TTC CGC GGC ATC TCC GCG GAC CAC TTC  1074
Arg Glu Ser Pro Gly Ala Ser Phe Arg Gly Ile Ser Ala Asp His Phe

GAG GCG GAG GTG GTG GAG CGC ACC GAC GTG TAC TAC TAC GAG ACG CGC  1122
Glu Ala Glu Val Val Glu Arg Thr Asp Val Tyr Tyr Tyr Glu Thr Arg

CCC GCT CTG TTT TAC CGC GTC TAC GTC CGA AGC GGG CGC GTG CTG TCG  1170
Pro Ala Leu Phe Tyr Arg Val Tyr Val Arg Ser Gly Arg Val Leu Ser

TAC CTG TGC GAC AAC TTC TGC CCG GCC ATC AAG AAG TAC GAG GGT GGG  1218
Tyr Leu Cys Asp Asn Phe Cys Pro Ala Ile Lys Lys Tyr Glu Gly Gly

GTC GAC GCC ACC ACC CGG TTC ATC CTG GAC AAC CCC GGG TTC GTC ACC  1266
Val Asp Ala Thr Thr Arg Phe Ile Leu Asp Asn Pro Gly Phe Val Thr
```

FIG. 1c

```
TTC GGC TGG TAC CGT CTC AAA CCG GGC CGG AAC AAC ACG CTA GGC CAG   1314
Phe Gly Trp Tyr Arg Leu Lys Pro Gly Arg Asn Asn Thr Leu Ala Gln

CCG CGG GCC CCG ATG GCC TTC GGG ACA TCC AGC GAC GTG GAG TTT AAC   1362
Pro Arg Ala Pro Met Ala Phe Gly Thr Ser Ser Asp Val Glu Phe Asn

TGT ACG GCG GAC AAC CTG GCC ATC GAG GGG GGC ATC AGC GAC CTA CCG   1410
Cys Thr Ala Asp Asn Leu Ala Ile Glu Gly Gly Met Ser Asp Leu Pro

GCA TAC AAG CTC ATG TGC TTC GAT ATC GAA TGC AAG GCG GGG GGG GAG   1458
Ala Tyr Lys Leu Met Cys Phe Asp Ile Glu Cys Lys Ala Gly Gly Glu

GAC GAG CTG GCC TTT CCG GTG GCC GGG CAC CCG GAG GAC CTG GTT ATT   1506
Asp Glu Leu Ala Phe Pro Val Ala Gly His Pro Glu Asp Leu Val Ile

CAG ATA TCC TGT CTG CTC TAC GAC CTG TCC ACC ACC GCC CTG GAG CAC   1554
Gln Ile Ser Cys Leu Leu Tyr Asp Leu Ser Thr Thr Ala Leu Glu His

GTC CTC CTG TTT TCG CTC GGT TCC TGC GAC CTC CCC GAA TCC CAC CTG   1602
Val Leu Leu Phe Ser Leu Gly Ser Cys Asp Leu Pro Glu Ser His Leu
                                                        ↓E
AAC GAG CTG GCG GCC AGG GGC CTG CCC ACG CCC GTG GTT CTG GAA TTC   1650
Asn Glu Leu Ala Ala Arg Gly Leu Pro Thr Pro Val Val Leu Glu Phe
        ↓E
GAC AGC GAA TTC GAG ATG CTG TTG GCC                               1677
Asp Ser Glu Phe Glu Met Leu Leu Ala
```

FIG. 1d

```
TTC ATG ACC CTT GTG AAA CAG TAC GGC CCC GAG TTC GTG ACC GGG TAC   48
Phe Met Thr Leu Val Lys Gln Tyr Gly Pro Glu Phe Val Thr Gly Tyr

AAC ATC ATC AAC TTC GAC TGG CCC TTC TTG CTG GCC AAG CTG ACG GAC   96
Asn Ile Ile Asn Phe Asp Trp Pro Phe Leu Leu Ala Lys Leu Thr Asp

ATT TAC AAG GTC CCC CTG GAC GGG TAC GGC CGC ATG AAC GGC CGG GGC  144
Ile Tyr Lys Val Pro Leu Asp Gly Tyr Gly Arg Met Asn Gly Arg Gly

GTG TTT CGC GTG TGG GAC ATA GGC CAG AGC CAC TTC CAG AAG CGC AGC  192
Val Phe Arg Val Trp Asp Ile Gly Gln Ser His Phe Gln Lys Arg Ser

AAG ATA AAG GTG AAC GGC ATG GTG AAC ATC GAC ATG TAC GGG ATC ATA  240
Lys Ile Lys Val Asn Gly Met Val Asn Ile Asp Met Tyr Gly Ile Ile
                            ↓ X
ACC GAC AAG ATC AAG CTC TCG AGC TAC AAG CTC AAC GCC GTG GCC GAA  288
Thr Asp Lys Ile Lys Leu Ser Ser Tyr Lys Leu Asn Ala Val Ala Glu

GCC GTC CTG AAG GAC AAG AAG AAG GAC CTG AGC TAT CGC GAC ATC CCC  336
Ala Val Leu Lys Asp Lys Lys Lys Asp Leu Ser Tyr Arg Asp Ile Pro

GCC TAC TAC GCC ACC GGG CCC GCG CAA CGC GGG GTG ATC GGC GAG TAC  384
Ala Tyr Tyr Ala Thr Gly Pro Ala Gln Arg Gly Val Ile Gly Glu Tyr

TGC ATA CAG GAT TCC CTG CTG GTG GGC CAG CTG TTT TTT AAG TTT TTG  432
Cys Ile Gln Asp Ser Leu Leu Val Gly Gln Leu Phe Phe Lys Phe Leu
```

FIG. 1e

```
CCC CAT CTG GAG CTC TCG GCC GTC GCG CGC TTG GCG GGT ATT AAC ATC   480
Pro His Leu Glu Leu Ser Ala Val Ala Arg Leu Ala Gly Ile Asn Ile

ACC CGC ACC ATC TAC GAC GGC CAG CAG ATC CGC GTC TTT ACG TGC CTG   528
Thr Arg Thr Ile Tyr Asp Gly Gln Gln Ile Arg Val Phe Thr Cys Leu

CTG CGC CTG GCC GAC CAG AAG GGC TTT ATT CTG CCG GAC ACC CAG GGG   576
Leu Arg Leu Ala Asp Gln Lys Gly Phe Ile Leu Pro Asp Thr Gln Gly

CGA TTT AGG GGC GCC GGG GGG GAG GCG CCC AAG CGT CCG GCC GCA GCC   624
Arg Phe Arg Gly Ala Gly Gly Glu Ala Pro Lys Arg Pro Ala Ala Ala

CGG GAG GAC GAG GAG CGG CCA GAG GAG GAG GGG GAG GAC GAG GAC GAA   672
Arg Glu Asp Glu Glu Arg Pro Glu Glu Glu Gly Glu Asp Glu Asp Glu

CGC GAG GAG GGC GGG GGC GAG CGG GAG CCG GAG GGC GCG CGG GAG ACC   720
Arg Glu Glu Gly Gly Gly Glu Arg Glu Pro Glu Gly Ala Arg Glu Thr
                                      ↓K
GCC GGC CGG CAC GTG GGC TAC CAA GGG GCC AAG GTC CTT GAC CCC ACT   768
Ala Gly Arg His Val Gly Tyr Gln Gly Ala Lys Val Leu Asp Pro Thr

TCC GGG TTT CAC GTG AAC CCC GTG GTG GTG TTC GAT CCC GCC AGC CTG   816
Ser Gly Phe His Val Asn Pro Val Val Val Phe Asp Pro Ala Ser Leu
```

FIG. 1f

```
TAC CCC AGC ATC ATC CAG GCC CAC AAC CTG TGC TTC AGC ACG CTC TCC    864
Tyr Pro Ser Ile Ile Gln Ala His Asn Leu Cys Phe Ser Thr Leu Ser

CTG AGG GCC GAC GCA GTG GCG CAC CTG GAG GCG GGC AAG GAC TAC CTG    912
Leu Arg Ala Asp Ala Val Ala His Leu Glu Ala Gly Lys Asp Tyr Leu

GAG ATC GAG GTG GGG GGG CGA CGG CTG TTC TTC GTC AAG GCT CAC GTG    960
Glu Ile Glu Val Gly Gly Arg Arg Leu Phe Phe Val Lys Ala His Val

CGA GAG AGC CTC CTC AGC ATC CTC CTG CGG GAC TGG CTC GCC ATG CGA   1008
Arg Glu Ser Glu Val Gly Gly Arg Arg Leu Phe Phe Val Lys Ala His

AAG CAG ATC CGC TCG CGG ATT CCC CAG AGC AGC CCC GAG GAG GCC GTG   1052
Val Arg Glu Ser Ser Arg Ile Pro Gln Ser Ser Pro Glu Glu Ala Val

CTC CTG GAC AAG CAG CAG GCC GCC ATC AAG GTC GTG TGT AAC TCG GTG   1104
Leu Leu Asp Lys Gln Gln Ala Ala Ile Lys Val Val Cys Asn Ser Val

TAC GGG TTC ACG GGA GTG CAG CAC GGA CTC CTG CCG TGC CTG CAC GTT   1152
Tyr Gly Phe Thr Gly Val Gln His Gly Leu Leu Pro Cys Leu His Val

GCC GCG ACG GTG ACG ACC ATC GGC CGC GAG ATG CTG CTC GCG ACC CGC   1200
Ala Ala Thr Val Thr Thr Ile Gly Arg Glu Met Leu Leu Ala Thr Arg

GAG TAC GTC CAC GCG CGC TGG GCG GCC TTC GAA CAG CTC CTG GCC GAT   1248
Glu Tyr Val His Ala Arg Trp Ala Ala Phe Glu Gln Leu Leu Ala Asp
```

FIG. 1g

```
TTC CCG GAG GCG GCC GAC ATG CGC GCC CCC GGG CCC TAT TCC ATG CGC   1296
Phe Pro Glu Ala Ala Asp Met Arg Ala Pro Gly Pro Tyr Ser Met Arg

ATC ATC TAC GGG GAC ACG GAC TCC ATA TTT GTG CTG TGC CGC GGC CTC   1344
Ile Ile Tyr Gly Asp Thr Asp Ser Ile Phe Val Leu Cys Arg Gly Leu

ACG GCC GCC GGG CTG ACG CCC ATG GGC GAC AAG ATG GCG AGC CAC ATC   1392
Thr Ala Ala Gly Leu Thr Ala Met Gly Asp Lys Met Ala Ser His Ile
                                        ↓X
TCG CGC GCG CTG TTT CTG CCC CCC ATC AAA CTC GAG TGC GAA AAG ACG   1440
Ser Arg Ala Leu Phe Leu Pro Pro Ile Lys Leu Glu Cys Glu Lys Thr

TTC ACC AAG CTG CTG CTG ATC GCC AAG AAA AAG TAC ATC GGC GTC ATC   1488
Phe Thr Lys Leu Leu Leu Ile Ala Lys Lys Lys Tyr Ile Gly Val Ile

TAC GGG GGT AAG ATG CTC ATC AAG GGC GTG GAT CTG GTG CGC AAA AAC   1536
Tyr Gly Gly Lys Met Leu Ile Lys Gly Val Asp Leu Val Arg Lys Asn

AAC TGC GCG TTT ATC AAC CGC ACC                                   1560
Asn Cys Ala Phe Ile Asn Arg Thr
```

FIG. 1h

| | | | | | | | | | | | | | | | | |
|---|---|---|---|---|---|---|---|---|---|---|---|---|---|---|---|---|
| TCC | AGG | GCC | CTG | GTC | GAC | CTG | CTG | TTT | TAC | GAC | GAT | ACC | GTA | TCC | GGA | 48 |
| Ser | Arg | Ala | Leu | Val | Asp | Leu | Leu | Phe | Tyr | Asp | Asp | Thr | Val | Ser | Gly | |
| GCG | GCC | GCC | GCG | TTA | GCC | GAG | CGC | CCC | GCA | GAG | GAG | TGG | CTG | GCG | CGA | 96 |
| Ala | Ala | Ala | Ala | Leu | Ala | Glu | Arg | Pro | Ala | Glu | Glu | Trp | Leu | Ala | Arg | |
| CCC | CTG | CCC | GAG | GGA | CTG | CAG | GCG | TTC | GGG | GCC | GTC | CTC | GTA | GAC | GCC | 144 |
| Pro | Leu | Pro | Glu | Gly | Leu | Gln | Ala | Phe | Gly | Ala | Val | Leu | Val | Asp | Ala | |
| CAT | CGG | CGC | ATC | ACC | GAC | CCG | GAG | AGG | GAC | ATC | CAG | GAC | TTT | GTC | CTC | 192 |
| His | Arg | Arg | Ile | Thr | Asp | Pro | Glu | Arg | Asp | Ile | Gln | Asp | Phe | Val | Leu | |
| ACC | GCC | GAA | CTG | AGC | AGA | CAC | CCG | CGC | GCG | TAC | ACC | AAC | AAG | CGC | CTG | 240 |
| Thr | Ala | Glu | Leu | Ser | Arg | His | Pro | Arg | Ala | Tyr | Thr | Asn | Lys | Arg | Leu | |
| GCC | CAC | CTG | ACG | GTG | TAT | TAC | AAG | CTC | ATG | GCC | CGC | CGC | GCG | CAG | GTC | 288 |
| Ala | His | Leu | Thr | Val | Tyr | Tyr | Lys | Leu | Met | Ala | Arg | Arg | Ala | Gln | Val | |
| CCG | TCC | ATC | AAG | GAC | CGG | ATC | CCG | TAC | GTG | ATC | GTG | GCC | CAG | ACC | CGC | 336 |
| Pro | Ser | Ile | Lys | Asp | Arg | Ile | Pro | Tyr | Val | Ile | Val | Ala | Gln | Thr | Arg | |
| GAG | CTA | GAG | GAG | ACG | GTC | GCG | CGG | CTG | GCG | GCC | CTC | CGC | GAG | CTA | GAC | 384 |
| Glu | Val | Glu | Glu | Thr | Val | Ala | Arg | Leu | Ala | Ala | Leu | Arg | Glu | Leu | Asp | |
| GCC | GCC | GCC | CCA | GGG | GAC | GAG | CCC | GCC | CCC | CCC | GCG | GCC | CTG | CCC | TCC | 432 |
| Ala | Ala | Ala | Pro | Gly | Asp | Glu | Pro | Ala | Pro | Pro | Ala | Ala | Leu | Pro | Ser | |
| CCG | GCC | AAG | CGC | CCC | CGG | GAG | ACG | CCG | TCG | CAT | GCC | GAC | CCC | CCG | GGA | 480 |
| Pro | Ala | Lys | Arg | Pro | Arg | Glu | Thr | Pro | Ser | His | Ala | Asp | Pro | Pro | Gly | |

FIG. 1i

```
GGC GCG TCC AAG CCC CGC AAG CTG CTG GTG TCC GAG CTG GCC GAG GAT    528
Gly Ala Ser Lys Pro Arg Lys Leu Leu Val Ser Glu Leu Ala Glu Asp

CCC GCA TAC GCC ATT GCC CAC GGC GTC GCC CTG AAC ACG GAC TAT TAC    576
Pro Ala Tyr Ala Ile Ala His Gly Val Ala Leu Asn Thr Asp Tyr Tyr

TTC TCC CAC CTG TTG GGG GCG GCG TGC GTG ACA TTC AAG GCC CTG TTT    624
Phe Ser His Leu Leu Gly Ala Ala Cys Val Thr Phe Lys Ala Leu Phe

GGG AAT AAC GCC AAG ATC ACC GAG AGT CTG TTA AAA AGG TTT ATT CCC    672
Gly Asn Asn Ala Lys Ile Thr Glu Ser Leu Leu Lys Arg Phe Ile Pro

GAA GTG TGG CAC CCC CCG GAC GAC GTG GCC GCG CGC CTC CGG GCC GCA    720
Glu Val Trp His Pro Pro Asp Asp Val Ala Ala Arg Leu Arg Ala Ala

GGG TTC GGG GCG GTG GGT GCC GGC GCT ACG GCG GAG GAA ACT CGT CGA    768
Gly Phe Gly Ala Val Gly Ala Gly Ala Thr Ala Glu Glu Thr Arg Arg

ATG TTG CAT AGA GCC TTT GAT ACT CTA GCA TGA GCC CCC CGT CGA AGC    816
Met Leu His Arg Ala Phe Asp Thr Leu Ala End

TGA TGT CCC TCA TTT TAC AAT AAA TGT CTG CGG CCG ACA CGG TCG GAA    864

TCT CCG CGT CCG TGG GTT TCT CTG CGT TGC GCC GGA CCA CGA GCA CAA    912
                                         ↓K
ACG TGC TCT GCC ACA CGT GGG CGA CGA ACC GGT ACC                    948
```

FIG. 1j

```
CCAAAAGGGT GTGGCCTAAC GAGCTGGGGG CGTATTTAAT CAGGCTAGCG CGGCGGGCCT    60
GCCGTAGTTT CTGGCTCGGT GAGCGACGGT CCGGTTGCTT GGGTCCCCTG GCTGCCATCA   120
AAACCCCACC CTCGCAGCGG CATACGCCCC CTCCGCGTCC CGCACCCGAG ACCCCGGCCC   180
GGCTGCCCTC ACCACCGAAG CCCACCTCGT CACTGTGGGG TGTTCCCAGC CCGCGTTGGG   240
   M  T  D  S  P  G  G  V  A  P  A  S  P  V  E  D  A  S  D  A  S  L   22
ATGACGGATTCCCCTGGCGGTGTGGCCCCCGCCTCCCCCGTGGAGGACGCGTCGGACGCGTCCCT   305
    G  Q  P  E  E  G  A  P  C  Q  V  V  L  Q  G  A  E  L  N  G  I  L  44
CGGGCAGCCGGAGGAGGGGGCGCCCTGCCAGGTGGTCCTGCAGGGCGCCGAACTTAATGGAATCCT   370
   Q  A  F  A  P  L  R  T  S  L  L  D  S  L  L  V  M  G  D  R  G  I   66
ACAGGCGTTTGCCCCGCTGCGCACGAGCCTTCTGGACTCGCTTCTGGTTATGGGCGACCGGGGCAT   435
      L  I  H  N  T  I  F  G  E  Q  V  F  L  P  L  E  H  S  Q  F  S  R  88
CCTTATCCATAACACGATCTTTGGGGAGCAGGTGTTCCTGCCCCTGGAACACTCGCAATTCAGTCG   500
      Y  R  W  R  G  P  T  A  A  F  L  S  L  V  D  Q  K  R  S  L  L  S 110
GTATCGCTGGCGCGGACCCACGGCGGCGTTCCTGTCTCTCGTGGACCAGAAGCGCTCCCTCCTGAG   565
```

FIG. 2a

```
        V   F   R   A   N   Q   Y   P   D   L   R   R   V   E   L   A   I   T   G   Q   A   P 132
      CGTGTTTCGCGCCAACCAGTACCCGGACCTACGTCGGGTGGAGTTGGCGATCACGGGCCAGGCCCC 630

F   R   T   L   V   Q   R   I   W   T   T   T   S   D   G   E   A   V   E   L   A   S 154
      GTTTCGCACGCTGGTTCAGCGCATATGGACGACGACGTCCGACGGCGAGGCCGTTGAGCTAGCCAG 695

E   T   L   M   K   R   E   L   T   S   F   V   V   L   V   P   Q   G   T   P   D   V 176
      CGAGACGCTGATGAAGCGCGAACTGACGAGCTTTGTGGTGCTGGTTCCCCAGGGAACCCCCGACGT 760

Q   L   R   L   T   R   P   Q   L   T   K   V   L   N   A   T   G   A   D   S   A   T 198
      TCAGTTGCGCCTGACGAGGCCGCAGCTCACCAAGGTCCTTAACGCGACCGGGGCCGATAGTGCCAC 825

P   T   T   F   E   L   G   V   N   G   K   F   S   V   F   T   T   S   T   C   V   T 220
      GCCCACCACGTTCGAGCTCGGGGTTAACGGCAAATTTTCCGTGTTCACCACGAGTACCTGCGTCAC 890

F   A   A   R   E   E   G   V   S   S   S   T   S   T   Q   V   Q   I   L   S   N   A 242
      CTTTGCTGCCCGCGAGGAGGGCGTGTCGTCCAGCACCAGCACCCAGGTCCAGATCCTGTCCAACGC 955

L   T   K   A   G   Q   A   A   A   N   A   K   T   V   Y   G   E   N   T   H   R   T 264
      GCTCACCAAGGCGGGCCAGGCGGCCGCCAACGCCAAGACGGTGTACGGGGAAAATACCCATCGCAC 1020

F   S   V   V   V   D   D   C   S   M   R   A   V   L   R   R   L   Q   V   G   G   G 286
      CTTCTCTGTGGTCGTCGACGATTGCAGCATGCGGGCGGTGCTCCGGCGACTGCAGGTCGGCGGGGG 1085
```

FIG. 2b

```
            T   L   K   F   F   L   T   T   P   V   P   S   L   C   V   T   A   T   G   P   N   A  308
         CACCCTCAAGTTCTTCCTCACGACCCCCGTCCCCAGTCTGTGCGTCACCGCCACCGGTCCCAACGC 1150

V   S   A   V   F   L   L   K   P   Q   K   I   C   L   D   W   L   G   H   S   Q   G   330
         GGTATCGGCGGTATTTCTCCTGAAACCCCAGAAGATTTGCCTGGACTGGCTGGGTCATAGCCAGGG 1215

S   P   S   A   G   S   S   A   S   R   A   S   G   S   E   P   T   D   S   Q   D   S  352
         GTCTCCTTCAGCCGGGAGCTCGGCCTCCCGGGCCTCTGGGAGCGAGCCAACAGACAGCCAGGACTC 1280

A   S   D   A   V   S   H   G   D   P   E   D   L   D   G   A   A   R   A   G   E   A  374
         CGCGTCGGACGCGGTCAGCCACGGCGATCCGGAAGACCTCGATGGCGCTGCCCGGGCGGGAGAGGC 1345

G   A   L   H   A   C   P   M   P   S   S   T   T   R   V   T   P   T   T   K   R   G  396
         GGGGGCCTTGCATGCCTGTCCGATGCCGTCGTCGACCACGCGGGTCACTCCCACGACCAAGCGGGG 1410

R   S   G   G   E   D   A   R   A   D   T   A   L   K   K   P   K   T   G   S   P   T   418
         GCGCTCGGGGGGCGAGGATGCGCGCGCGGACACGGCCCTAAAGAAACCTAAGACGGGGTCGCCCAC 1475

A   P   P   P   A   D   P   V   P   L   D   T   E   D   D   S   D   A   A   D   G   T   440
         CGCACCCCCGCCCGCAGATCCAGTCCCCCTGGACACGGAGGACGACTCCGATGCGGCGGACGGGAC 1540

A   A   R   P   A   A   P   D   A   R   S   G   S   R   Y   A   C   Y   F   R   D   L   462
         GGCGGCCCCGTCCCGCCGCTCCAGACGCCCGGAGCGGAAGCCGTTACGCGTGTTACTTTCGCGACCT 1605

P   T   G   E   A   S   P   G   A   F   S   A   F   R   G   G   P   Q   T   P   Y   G  484
         CCCGACCGGAGAAGCAAGCCCCGGCGCCTTCTCCGCCTTCCGGGGGGCCCCCAAACCCCGTATGG 1670

F   G   F   P   -                                                                    488
         TTTTGGATTCCCCTGACGGGGCGGGGCCTTGGCGGCCGCCCAACTCTCGCACCATCCCGGGTTAAT 1735

GTAAATAAACTTGGTATTGCCCAACACTTTCCCGCGTGTCGCG                                            1778
```

FIG. 2c

UL42 ORF
Wild Type
(488 aa)
ΔC341
ΔC260
FIG.6

INHIBITORS OF HERPES SIMPLEX VIRUS REPLICATION

This invention was made with Government support, and the U.S. Government therefore has certain rights in the invention.

BACKGROUND OF THE INVENTION

This invention relates to inhibition of viral replication, particularly, Herpes Simplex Virus.

Herpes Simplex Virus (HSV) and other herpesviruses are important human pathogens. These viruses encode several proteins that are required for the replication of their DNA (Wu et al., 1988, J. Virol. 62:435; Weller et al., 1988, Eukaryotic DNA Replication, 6; 53, Cold Spring Harbor, N.Y.). The principal enzyme of herpesvirus replication is a virus-encoded DNA polymerase, whose DNA sequence has been reported (Quinn et al., 1985, Nucleic Acids Res. 13:8143; Gibbs et al., 1985, Proc. Nat. Aca. Sci. 82:7679). Drugs that inhibit herpesvirus DNA polymerase activity, for example, acyclovir, have been used to prevent viral DNA replication.

UL42, also known as 65K DNA binding protein, is another HSV protein required for viral DNA replication. UL42 has double-stranded DNA binding activity and has been found to be associated with HSV DNA polymerase (Powell et al., 1977, J. Virol. 24:618; Gallo et al., 1988, J. Virol. 62:2874; Gallo et al., 1989, J. Virol. 63:5023).

SUMMARY OF THE INVENTION

The invention provides for inhibition of HSV infection by means of an inhibitor capable of preventing the formation of an HSV DNA polymerase:UL42 replication complex, which is required for viral DNA replication. The invention is based in part on our discovery of the region of the HSV polymerase molecule which binds to UL42.

The invention also features an immunoassay for identifying an inhibitor of HSV DNA replication that includes the steps of 1) providing a DNA polymerizing complex including the two complex members, HSV DNA polymerase and UL42, or binding fragments thereof, which may include protein fragments expressed from cloned DNA fragments, proteolytic fragments, or synthetic peptides; 2) providing a potential inhibitor that inhibits binding of HSV DNA polymerase to Ul42; 3) mixing the complex members in the presence of the potential inhibitor, and 4) determining whether the potential inhibitor inhibits formation of the complex.

In preferred embodiments, the immunoassay further includes providing an antibody specific for one of the complex members, wherein at least one of the members is labeled, and formation of the complex is determined by immunoprecipitation of the labeled complex.

The invention also features a method of assaying a potential inhibitor for the ability to inhibit UL42-stimulated HSV DNA polymerase activity, the method including 1) providing a DNA polymerization mixture including HSV DNA polymerase, UL42, and the potential inhibitor that inhibits binding of HSV DNA polymerase to UL42; 2) incubating the mixture for a time sufficient to allow polymerase activity to occur; and 3) measuring DNA polymerase activity as an inverse measure of inhibition.

In another aspect, the invention features a method of assaying a potential inhibitor for the ability to inhibit HSV infection, the method including 1) providing HSV and cells capable of being infected with HSV; 2) introducing into the cells, separately or together, DNA encoding a potential inhibitor of HSV replication that inhibits binding of HSV DNA polymerase to UL42, and part or all of the HSV genome, wherein the inhibitor may be an HSV DNA polymerase fragment or a fragment of UL42; and 3) determining whether the inhibitor inhibits HSV production in the cells.

The inhibitors of the invention can be used for treating a patient infected with HSV.

In preferred embodiments, the inhibitor includes an HSV DNA polymerase fragment, preferably derived from the carboxy-terminal half of the polymerase molecule, e.g., from a 227 amino acid region situated between residues 1008 and 1235 of the polymerase, from a 162 amino acid region between residues 1073 and 1235 of the polymerase.

As used herein, "derived from" means the amino acid sequence of the fragment is substantially identical to the natural sequence, and is made by peptide synthesis, proteolysis of the corresponding protein or a portion thereof, or is produced from a cloned DNA fragment. "Substantially identical" means identical at at least 70% of the sequence positions, e.g., nucleotides or amino acids; i.e., any deletions to or modifications of the sequence which result in a sequence having 70% homology with the natural sequence.

In other preferred embodiments, the amino acid sequence of the inhibitor is derived from a portion of UL42; preferably, the potential inhibitor includes a UL42 fragment which may be derived from the amino terminal half of the UL42 molecule.

In other preferred embodiments, the inhibitor is a 200 amino acid fragment; more preferably, a 100 amino acid fragment; most preferably, a 10 to 30 amino acid fragment derived from the carboxy terminal half of HSV DNA polymerase or the amino terminal half of UL42.

Other features and advantages of the invention will be apparent from the following description of the preferred embodiments thereof, and from the claims.

DESCRIPTION OF PREFERRED EMBODIMENTS

Before describing preferred embodiments of the invention, the drawings will be briefly described.

DRAWINGS

FIGS. 1a, 1b, 1c, 1d, 1e, 1f, 1g, 1g, 1i, 1j are the DNA sequence of the HSV DNA polymerase gene, from Gibbs et al., supra.

FIGS. 2a, 2b, 2c is the DNA sequence of the UL42 gene, from McGeoch et al., 1988, J. Virol. 62:444.

FIG. 6 is a diagram of UL42 deletion fragments.

HSV REPLICATION

Figure 3:
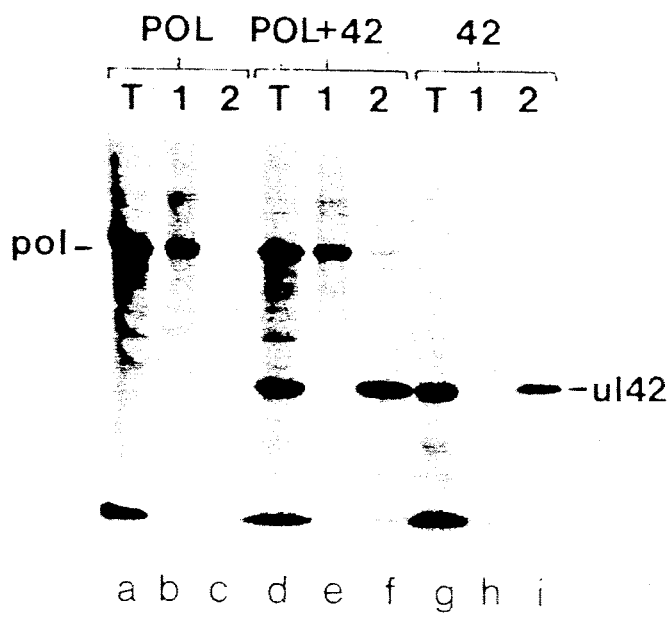
FIG. 3 is an autoradiogram of an HSV DNA polymerase:UL42 binding assay.

Herpes Simplex Virus encodes at least seven proteins that are essential for DNA replication, two of which are the viral DNA polymerase and the product of the UL42 gene. The UL42 protein is a 65 kDa DNA binding protein which has been shown to copurify with the polymerase through chromatographic procedures and to stimulate polymerase activity in vitro. The invention provides methods of identifying inhibitors of HSV infection by interference with viral replication. As is described below, the invention depends in part on defining the sites of interaction on both the HSV DNA polymerase molecule and the UL42 molecule, and identifying protein fragments or peptides which inhibit formation of the HSV DNA polymerase:UL42 complex, HSV DNA polymerase activity, and production of HSV by virus-infected cells; these methods are useful for providing inhibitors for treating a patient infected with HSV.

The Regions of HSV DNA
Polymerase:UL42 Interaction

Inhibitors of HSV DNA replication will interfere with viral DNA replication by inhibiting the binding of HSV DNA polymerase to UL42. The amino acid sequence of protein or peptide inhibitors are chosen so as to mimic the sequence of the region of either polymerase or UL42. The regions of the polypeptides that interact with each other are the carboxy terminal portion of HSV DNA polymerase and the amino terminal or middle portions of UL42. These regions were shown to interact with each other as follows.

The UL42 and HSV DNA polymerase (pol) genes or portions of the genes were cloned into plasmids such that these genes or portions thereof are efficiently transcribed with a bacteriophage RNA polymerase. The DNA sequences of the HSV DNA polymerase gene and the UL42 gene are shown in FIGS. 1a-1j and 2a-2c respectively; the HSV DNA polymerase gene encompasses approximately 4080 nucleotides and the UL42 gene 1464 nucleotides, respectively. Expression vectors containing these genes were constructed as follows. In FIGS. 1(a) 1(c), the boxed sequences are sufficient to interact with UL42, and sequences beyond the line at 1073 are necessary for the interaction.

Transcription vector plasmids pINGUL30 and pINGUL42, encoding pol and UL42, respectively, were constructed by inserting cloned copies of each gene into the plasmid pING14.1. Plasmid pING14.1 was constructed by inserting a small DNA fragment containing, in order, recognition sites for the restriction enzymes BglII, PvuII, NcoI, EcoRV, PstI, and HindIII into the BglII site of plasmid pSP64 T (Krieg, P. A., and Melton, D. A. (1984). Nucleic Acids Res. 12, 7057) pING14.1 contains a bacteriophage SP6 RNA polymerase promoter. Briefly, a modified polymerase gene lacking the short open reading frame (ORF) upstream of the pol ORF was excised from plasmid pDP47 using the restriction enzymes HindIII and XbaI. pDP47 consists of the entire pol ORF and 65 nucleotides of the 51 non coding sequence (Yager et al., 1988, J. Virol. 62:2007) cloned into plasmid pGEM42 (Promega Biotech, Madison, WI). The excised pol fragment was then treated with the Klenow fragment of DNA polymerase to fill in 5' overhanging ends and ligated into PvuII digested pING14.1 to generate plasmid pINGUL30. Similarly, pINGUL42 was created by excising the UL42 gene from plasmid pL42 with enzymes RsrII and EcoRI, followed by end filling and ligation into PvuII digested pING14.1. Plasmid pL42 was constructed by inserting the 2.9 kb PvuI DNA fragment between nucleotides 92391 and 95302 of the unique long section of the HSV genome (McGeoch et al., (1988). J. Gen. Virol. 69, 1531) into the EcoRI site of plasmid pGEM3Zf(+) (Promega) after the addition of EcoRI linkers.

Plasmids encoding deleted versions of the pol and UL42 genes were then created by manipulation of the wild type genes inserted in pINGUL30 and pINGUL42, respectively. Candidate inhibitor protein fragments or peptides will be derived from some of these polymerase deletion fragments. The deletions were created by restriction enzyme digestion of cloned DNA; however, any suitable method may be used, e.g., nuclease digestion. Amino-terminal deletions are numbered according to the first amino acid residue of the pol or UL42 protein encoded by the deleted gene, while carboxy-terminal deletions are numbered according to the last residue present Internal deletions are numbered according to the amino acids missing. Nucleotide residues are numbered from the A of the first ATG codon of the ORF.

Polymerase deletion plasmids, which are shown diagramatically in FIG. 5, were created as follows. ∇C1072 was created by removing sequences downstream of the BamHI site at position 3211. ∇C1008 was treated by removing sequences downstream of the PstI site at position 3021. ∇C907 was created by removing sequences downstream of the NcoI site at position 2710. ∇350-477 was created by removing sequences between the BalI sites at positions 1050 and 1428. ∇316-697 was created by removing sequences between the KpnI sites at positions 946 and 2086. ∇331-973 was created by removing sequences between the ApaI sites at positions 992 and 3419. ∇203-577 was created by removing sequences between the ScaI sites at positions 608 and 1727. ∇222-477 was created by removing sequences between the BglII site at position 665 and the BalI site at position 1428. ∇222-960 was created by removing sequences between the BglII site at position 665 and the FspI site at position 2874. ∇N1008 was created by removing sequences upstream of the PstI site at position 3021; in this construct, an in-frame ATG codon was supplied by the vector sequences.

UL42 deletion plasmids, shown diagramatically in FIG. 6, were created as follows. ∇C341 was constructed by removing sequences downstream of the SmaI site at position 1027, while ∇C269 was created by removing sequences downstream of SalI site at position 806.

Protein fragments encoded by the polymerase and UL42 deletion plasmids described above were synthesized in vitro as follows. Uniformly sized capped synthetic mRNAs encoding pol, UL42, or fragments thereof, were generated by in vitro transcription of the appropriate plasmid (linearized downstream of the ORF with the restriction enzyme HindIII), using the bacteriophage SP6 RNA polymerase transcription system (Promega Biotech, Madison, Wis.), in the presence of a molar excess of RNA cap analog (m$^7$GpppG) (New England Biolabs, Beverly, Mass.), according to standard procedures (Melton et al., 1984, Nucleic Acids Res. 12:7035).

Individual or mixed transcripts were then translated in a micrococcal nuclease-treated rabbit reticulocyte lysate system (Promega) according to the manufacturers instructions, except that the reactions were incubated at 37° instead of 30°, at a final mRNA concentration of 1-10ng/μl, in the presence of 2μCi/μl [$^{35}$S]-methionine (specific activity > 800 Ci/mmol) (New England Nuclear, Boston, Mass.). The radiolabeled UL42 polypeptide and the wild type or deleted polymerase polypeptide are detectable and resolved readily using SDS polyacrylamide gel electrophoresis. Each protein fragment was then tested for binding in the following reconstitution system.

Immunoassay for Identifying Inhibitor

Candidate inhibitor protein fragments or peptides may be tested in an immunoassay which includes HSV DNA polymerase, or a UL42-binding fragment thereof, and UL42, or a polymerase binding fragment thereof, and an antibody specific for polymerase or UL42. Prior to adding the candidate inhibitor, a control experiment is performed in which an HSV DNA polymerase or a polymerase derived protein fragment is tested for ability to bind UL42, and UL42 or a UL42-derived fragment is tested for ability to bind polymerase by combining the fragment and its cognate protein to allow complex formation and immunoprecipitating the complexed or uncomplexed proteins or fragments using either HSV DNA polymerase-specific antibody or UL42-specific antibody. Antiserum specific for HSV DNA polymerase or UL42 can be made according to conventional techniques, using purified pol or UL42 as the immunogen. Polyclonal rabbit antisera to two defined regions of the herpes simplex virus (HSV) type 1 strain KOS DNA polymerase (pol) are described by Yager et al., 1990, J. Virol. 64, in press. Polyclonal rabbit antisera to the HSV UL42 protein are described by Olivo et al, 1989, J. Virol. 63:196.

The antiserum bound molecules are then precipitated using S. aureus protein A and the complexes washed to remove non-specifically bound material. Immunoprecipitations are carried out by diluting 1-5 µl of reticulocyte lysate in 100 µl of immunoprecipitation (IP) buffer (100 mM KCl, 50 mM Tris-Cl pH 7.6, 5 mM $MgCl_2$, 0.1% NP40, 1 mM phenylmethylsulphonylfluoride), followed by the addition of 2 µl of antisera and 50 82 1 of a 10% (w/v) slurry of protein-A sepharose (Sigma Chem. Co., St. Louis, Mo.) in IP buffer. This mixture is then incubated overnight at 4° with gentle rotation. The next day, the sepharose beads are collected by micro-centrifugation, washed twice with 750 µl of IP buffer, and once with 750 µl of low SDS IP buffer (containing 0.1% SDS, 1% sodium deoxycholate, 1% Triton X-103 in place of the 0.1% NP40), after which bound proteins are eluted in 40 µl of Laemmli's sample buffer (Laemmli, 1970, Nature, 227:680. The immunoprecipitates are then resolved on a polyacrylamide gel and the gel is subject to autoradiography.

A candidate inhibitor peptide is added to the above described binding reaction in order to test for inhibition of UL42:polymerase complex formation.

Defining the UL42-Binding Site on HSV DNA Polymerase

The portion of HSV DNA polymerase that interacts with UL42 during DNA replication was identified using the polymerase:UL42 complex in vitro reconstitution system described generally above. Polymerase fragments that result in complex formation, i.e., those fragments derived from the carboxy terminus of the protein, are candidates for inhibitors of replication because they will interfere with binding of polymerase and UL42 and thus prevent HSV DNA replication. The polymerase fragments diagrammed in FIG. 5 were tested in the following reconstitution system for binding to UL42. This system is also used to test for inhibition of binding by including polymerase and UL42 in addition to the candidate inhibitor, because the reconstitution system results in detection of an interaction or a lack of interaction between UL42 and polymerase or a polymerase fragment. Precipitates formed with antiserum specific for UL42 will not only contain UL42, but will also contain polymerase polypeptides. Similarly, precipitates formed with antiserum specific for polymerase will not only contain polymerase, but will also contain UL42. Results of binding assays for different polymerase fragments are as follows.

FIG. 3 is an autoradiogram showing results of an experiment in which stable complexes between wild type polymerase fragments and UL42 were detected. Transcripts encoding full-length polymerase and UL42 were translated either singly or together, and then aliquots of the reactions were subject to polyacrylamide gel electrophoresis either before (T) or after immunoprecipitation with monospecific anti polymerase (1) or anti UL42 (2) sera. The immunoprecipitations of singly translated polypeptides provide controls for specificity of the antisera; when polymerase is translated alone, it is only precipitated by anti polymerase antiserum (lane b), and not by anti UL42 antiserum (lane c). Similarly, when UL42 is translated alone, it is only precipitated by anti UL42 antiserum (lane i), and not by anti-polymerase antiserum. When the two proteins are co translated (lanes d f), it can be seen that both polypeptides are precipitated by antiserum to either polypeptide (lanes e and f). This specific coprecipitation provides evidence of a stable interaction between the two proteins.

Figure 4A:
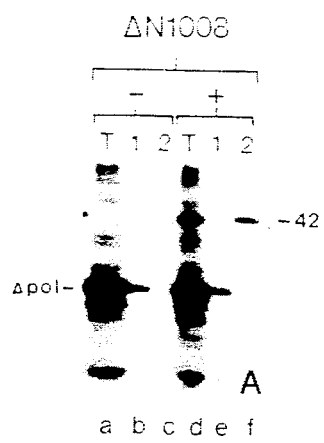
FIGS. 4A, 4B, 4C are polymerase:UL42 binding assays in which three polymerase deletion fragments were tested.
Figure 4B:
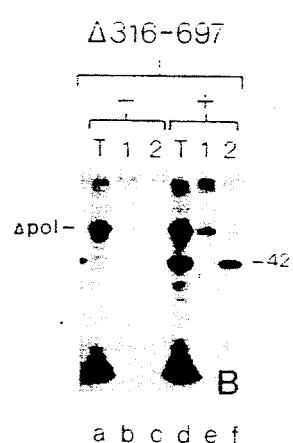
Figure 4C:
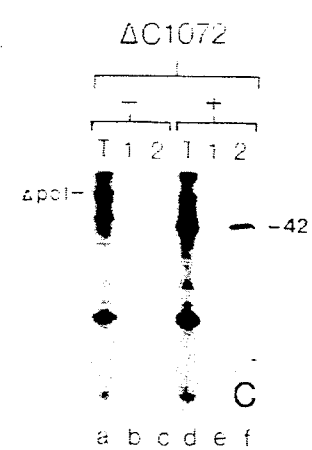

The UL42-binding site on HSV DNA Polymerase was determined by creating deletions in the polymerase gene; the corresponding protein fragments encoded by these constructs were produced and tested for their ability to bind UL42 in the reconstitution assay described above. FIG. 4 shows results obtained for three such fragments. As described above, the polymerase mRNAs were translated either alone (−), or together (+) with Ul42; aliquots of the translations were then analyzed by polyacrylamide gel electrophoresis before (T) or after immunoprecipitation with antiserum specific for polymerase (1) or UL42 (2).

FIG. 4, panel A, shows results obtained with the largest deletion of polymerase examined (∇N1008), in which only the carboxy terminal 227 amino-acids remain (∇pol in FIG. 4). As expected, when translated alone (lanes a-c), the polymerase fragment is only precipitated by anti-polymerase antiserum (lane b), and not by anti UL42 antiserum (lane c). However, when the ∇N1008 polymerase fragment was co-translated with UL42 (lanes d-f), the ∇pol fragment is precipitated by anti UL42 (lane f). Conversely, UL42 coprecipitates with the ∇pol fragment (lane e). This experiment indicates that the carboxy terminal 18% of polymerase is sufficient to bind UL42.

FIG. 4, panel B, shows results obtained with an internal deletion of polymerase (∇316-697), in which sequences coding for amino acids 316 to 697 have been removed. The results show that this ∇pol fragment is not precipitated by anti-UL42 antiserum in the absence of UL42 itself (lane c), but does co precipitate with UL42 when the pol fragment is translated together with UL42 (lane f). These results are consistent with those obtained for the ∇N1008 polymerase fragment. In addition, UL42 co-precipitates with the ∇316-697 polymerase fragment (lane e).

FIG. 4, panel C, shows the results obtained with the smallest carboxy-terminal deletion examined (∇C1072), in which only the last 163 amino acids have been deleted. As before, the ∇pol fragment is only precipitated by anti polymerase antiserum (lane b), and not by anti UL42 antiserum (lane c) when translated alone. However, when cotranslated with UL42 (lanes d-f), the ∇pol fragment is precipitated by anti-polymerase antiserum (lane e), but not by anti-UL42 antiserum (lane f). These results indicate that the loss of a small portion of the carboxy-terminus of polymerase is sufficient to destroy the binding of UL42 in this assay, a result which is consistent with the observation that the carboxy-terminus alone is sufficient for the interaction.

Figure 5:
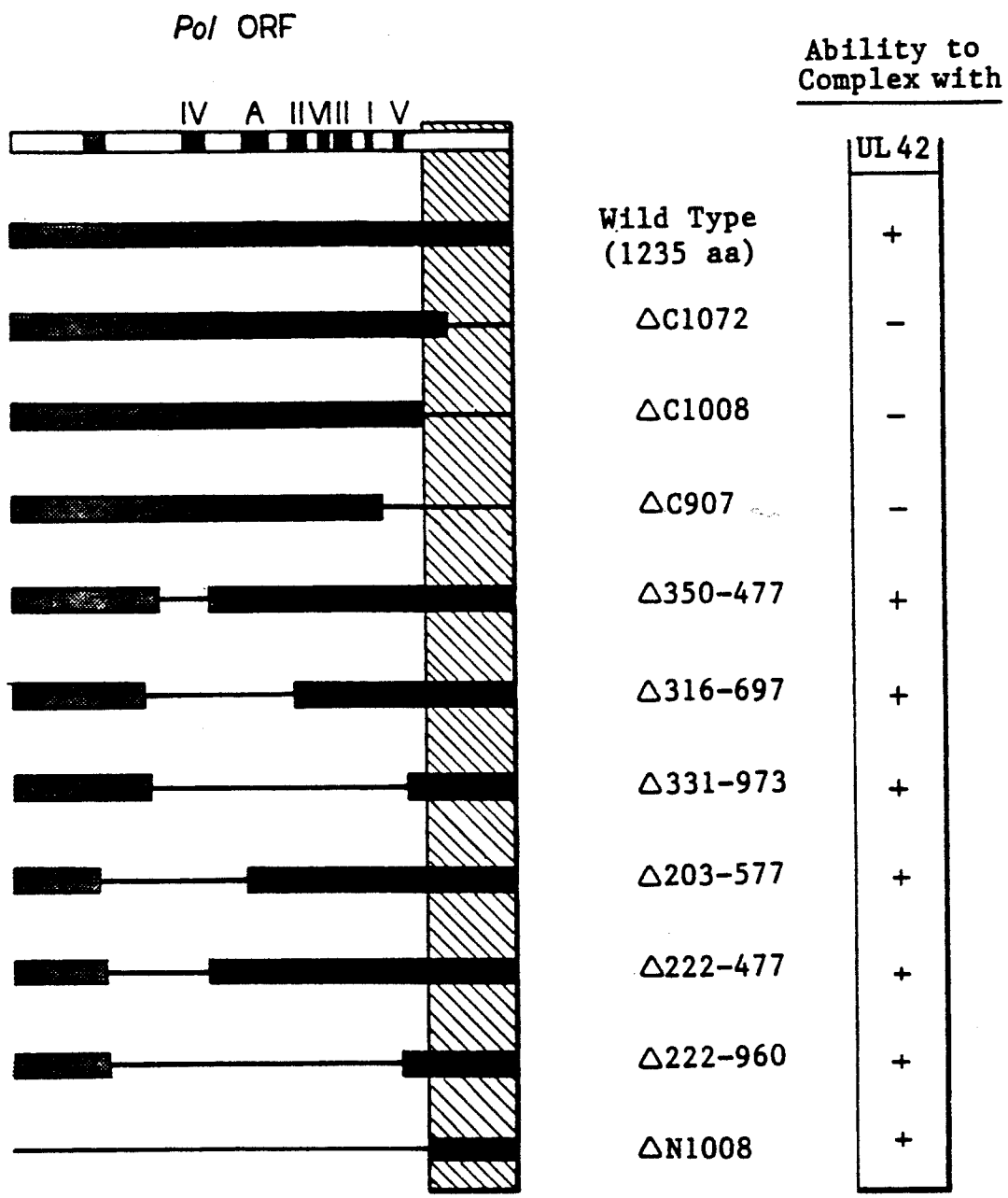
FIG. 5 is a diagram of results obtained in binding assays for various polymerase deletion fragments.

The UL42-binding activities of the polymerase fragments and several others are summarized in FIG. 5. The polymerase ORF is represented by the shaded rectangles, deleted regions of the polymerase are represented as lines, and previously identified regions of sequence similarity between the HSV DNA polymerase and other DNA polymerases (Gibbs et al., 1988, supra) are indicated at the top of FIG. 5. The results presented in FIG. 5 show that any deletion which leaves the carboxy-terminal 227 amino-acids intact does not affect polymerase binding, while deletions which wholly or partially eliminate this region destroy the interaction. The results are consistent with the conclusion that a UL42-binding domain of polymerase is contained within the region of the polymerase encompassed by amino acids 1008 to 1235, and that amino-acids downstream of residue 1072 are necessary for a stable interaction.

The region of the HSV DNA polymerase that is sufficient to interact with UL42 is boxed in FIG. 1. The complete boxed sequence runs from amino acid 1008 in the predicted polymerase polypeptide to the carboxyl-terminal amino acid (amino acid 1235). There is a line at amino acid 1073; some sequences between this amino acid and the carboxy-terminal amino acid are necessary for the interaction with UL42, since their deletion prevents the interaction. A candidate inhibitor protein fragment or peptide having amino acid sequence which mimics the polymerase carboxy terminal sequence is derived from the region downstream of residue 1008 of the polymerase protein.

The Polymerase-Binding Site on UL42

The polymerase binding site on UL42 lies in the amino terminal or middle of the UL42 polypeptide, as shown diagramatically in FIG. 6; candidate inhibitors that bind the polymerase molecule by mimicking the UL42 molecule are derived from these regions of the UL42 molecule. The region will be further defined by creating deletions of UL42 spanning this region of the protein and will be constructed as described above for the polymerase protein. Each deletion will then be assayed for its ability to form a complex with HSV DNA polymerase (or one of the C-terminal polymerase fragments) that is immunoprecipitable by anti-polymerase or anti-UL42 antisera.

FIG. 6 shows in diagrammatic form two UL42 fragments which were constructed and tested. The result of this binding experiment show that at least the larger of these deletions (∇C260) is capable of binding wild type HSV DNA polymerase, a result which is consistent with the conclusion that the polymerase-binding region of UL42 lies towards the middle or amino-terminus of the protein.

By more specifically defining the polymerase:UL42 sites of interaction, smaller candidate inhibitors may be identified. Other peptides will also be candidate inhibitors, for example, peptides derived from the carboxy terminus of HSV DNA polymerase and the middle or amino terminal portion of UL42 by linker-scanning (McKnight et al., 1982, Science 217:316), linker insertion e.g., (Lobel et al., 1984, Proc. Nat. Aca. Sci. 81:4149), or point mutagenesis (e.g., Taylor et al., 1985, Nucleic Acids Res. 13:8765) of the protein or protein fragment. These procedures are well-known in the art. A candidate peptide inhibitor having an amino acid sequence derived from either the polymerase or UL42 binding regions will be able to bind to the cognate protein and will be capable of inhibiting UL42:polymerase complex formation and thus viral DNA replication or infection. Inhibitors will be tested according to one or more of the methods of the invention described below.

In the test for inhibition of HSV DNA polymerase-:UL42 complex formation, the inhibitor is present during the co-translation and subsequent immunoprecipitation steps of the reconstitution assay described above. If an inhibitor prevents reconstitution of the complex, control experiments will indicate whether inhibition of complex formation is due to inhibition of complex formation, or to other factors, e.g., translation of mRNAs, or co precipitation of molecules unrelated to polymerase or UL42.

Inhibition of HSV DNA Polymerase Activity

A candidate inhibitor can be tested to determine if it inhibits HSV DNA polymerase activity by adding the inhibitor to a polymerization mix that contains HSV DNA polymerase, UL42, a mixture of nucleotides containing at least one labeled nucleotide and a primer DNA template, such as M13 phage DNA and a sequencing primer. The mixture is incubated for a time sufficient to allow polymerization to occur and polymerase activity, or lack of activity, is detected by determining the amount of incorporation of the labeled nucleotide. DNA polymerization assays are well-known in the art (see, for example, Maniatis et al., eds., Molecular Cloning, A Laboratory Manual, Cold Spring Harbor, N.Y., 1982) and have been optimized for HSV DNA polymerase (e.g., Elias et al., 1986, Proc. Nat. Aca. Sci. 83:6322). Control polymerization assays will be performed in order to determine if the inhibitor directly inhibits HSV DNA polymerase activity by adding the inhibitor to a mixture that contains the polymerase but lacks UL42. Residual DNA polymerase activity that occurs in the absence of UL42 will be detectable in the absence of inhibition. If polymerase activity is inhibited in the absence of UL42, then the inhibitor directly inhibits polymerase activity. The potential inhibitor can also be tested to determine if inhibition is specific for HSV DNA polymerase by testing for inhibition of other DNA polymerases, e.g., E. coli DNA polymerase I, or T7 or T4 phage DNA polymerases.

Inhibiton of HSV Infection in Cultured Cells

A candidate inhibitor will be tested for ability to inhibit HSV infection in cultured cells as follows. A cloned portion of the HSV DNA polymerase gene encoding a potential inhibitor fragment, or a cloned DNA fragment encoding a potential inhibitor peptide, will be inserted into an expression vector and introduced into cells capable of being infected with HSV, along with infectious HSV DNA, according to conventional procedures, e.g., by transfection. Inhibition of HSV infection will be determined by inhibiton of plaque formation according to conventional procedures. Alternatively, the same cloned DNA fragment will be inserted into an appropriate expression vector and introduced into viral-free cells to create a cell line that carries the DNA fragment and expresses the encoded protein fragment or peptide. The creation of stably transformed cell lines is described by DeLuca et al. (1985, J. Virol. 56:558). The stable cell line can then be tested for the ability to resist HSV infection using plaque or burst assays, according to conventional procedures. Alternatively, the inhibitor protein fragment or peptide may be added to virus-infected cell cultures by scrape-loading the cells (Fechheimer et al., 1987, Proc. Nat. Aca. Sci. 84:8463), since certain proteins or peptides can be directly taken up by cells (Frankel et al., 1988, Cell 55:1189; Green et al., 1988, Cell 55:1179; and Meek et al., 1990, Nature 343:90), and thus inhibit production of virus.

Finally, the protein fragment or peptide inhibitor can be tested for its ability to inhibit viral replication and pathogenesis, and tested for toxicity, in animal models according to standard methods.

Non-Peptide Inhibitors

An anti-herpes virus drug can be derived from a peptide inhibitor identified by one or more of the tests described above as follows. The shortest peptide with good activity in the test will first be identified. Information about its chemistry and conformation can be predicted from the primary amino acid sequence of the peptide. Structural studies of the peptide, longer versions of the peptide, or the peptide complexed with either HSV DNA polymerase or UL42 may be performed using biophysical methods that are well-known in the art, such as nuclear magnetic resonance or X-ray diffraction. Computer-aided molecular modeling will be useful in understanding the chemical and physical properties of the peptide. From this information, non-peptide derivatives of the peptide inhibitor may be synthesized which will have useful pharmacological properties (e.g., long serum half-life); these derivatives will then be tested in the tests described above in place of the peptide. The structure and conformation of a non peptide derivative will then be analysed using some of the techniques used to analyze peptide structure and comformation, and new derivatives will be synthesized to improve upon the first generation drugs. Third or fourth, etc., generation drugs will then be synthesized to maximize potency and efficacy.

Derivation of non-peptide inhibitors from peptides has been accomplished for substrates or inhibitors of medically important enzymes, such as angiotensin converting enzyme or human immunodeficiency virus protease (Dreyer et al., 1989, Proc. Nat. Aca. Sci. 86:9752; Meek et al., 1990, supra), while others have served as ligands or inhibitors of certain important receptors, such as the receptor for substance P.

Mechanism of Action

The mechanism of inhibition is unknown. Peptides or non-peptide inhibitors of the invention may prevent herpes virus infection in a mammal, particularly a human patient, by acting as an inhibitor of viral DNA replication by a number of mechanisms, e.g., an HSV polymerase-derived or a UL42 derived peptide or non-peptide inhibitor may competitively inhibit the binding of UL42 to HSV polymerase, or the inhibitor may bind to one of the proteins and cause a conformational change which prevents the complex from forming; thus, UL42-dependent stimulation of viral DNA replication may be prevented.

Use

Methods of the invention are useful for identifying inhibitors of HSV DNA replication, or for treating HSV infection. Peptide or non peptide inhibitors of the invention may be used directly in the testing systems described above or may be administered to a mammal, particularly a human, in one of the traditional modes (e.g., orally, parenterally, transdermally, or transmucosally), in a sustained release formulation using a biodegradable biocompatible polymer, or by on-site delivery using micelles, gels and liposomes, or rectally (e.g., by suppository or enema). The analogs can be administered to a human patient in a dosage of 0.25 $\mu$g/kg/day to 5 mg/kg/day.

Other embodiments are within the following claims.
What is claimed is:

1. A method of identifying an inhibitor of herpes simplex virus, HSV, DNA replication comprising the steps of
   (1) providing a mixture comprising HSV DNA polymerase and UL42, or fragments thereof, capable of forming a complex,
   (2) providing a potential inhibitor that inhibits binding of said HSV DNA polymerase to said UL42,
   (3) mixing said HSV DNA polymerase and said UL42 in the presence of said inhibitor, and
   (4) determining whether said potential inhibitor inhibits formation of said complex.

2. The method of claim 1, further comprising providing an antibody specific for either said HSV DNA polymerase or said UL42, wherein one of said HSV DNA polymerase or said UL42 is labeled and formation of said complex is determined by immunoprecipitation of said complex.

3. The method of claim 1, said potential inhibitor being derived from an HSV DNA polymerase fragment.

4. The method of claim 3 wherein said fragment is derived from the carboxy terminal portion of said polymerase molecule.

5. The method of claim 4 wherein said fragment is derived from a 227 amino acid region situated between residues 1008 and 1235 of said polymerase.

6. The method of claim 4 wherein said fragment is derived from a 162 amino acid region situated between residues 1073 and 1235 of said polymerase.

7. The method of claim 1 wherein the amino acid sequence of said potential inhibitor is derived from a fragment of said UL42.

8. The method of claim 1 wherein said potential inhibitor comprises a UL42 fragment.

9. The method of claim 8 wherein said fragment is derived from the amino terminal half of said UL42 molecule.

10. A method of assaying a potential inhibitor for the ability to inhibit UL42-stimulated HSV DNA polymerase activity, said method comprising the steps of
    (1) providing a DNA polymerization mix comprising HSV DNA polymerase, UL42, and a potential inhibitor that inhibits binding of HSV DNA polymerase to UL42,
    (2) incubating said mix for a time sufficient to allow said polymerase activity to occur, and (3) measuring said DNA polymerase activity, as an inverse measure of inhibition.

11. The method of claim 10 wherein said potential inhibitor is derived from an HSV DNA polymerase fragment.

12. The method of claim 11 wherein said fragment is derived from the carboxy terminal half of said polymerase molecule.

13. The method of claim 10 wherein said fragment is derived from a 227 amino acid region situated between residues 1008 and 1235 of said polymerase.

14. The method of claim 10 wherein said fragment is derived from a 162 amino acid region situated between residues 1073 and 1235 of said polymerase.

15. The method of claim 10 wherein the amino acid sequence of said potential inhibitor is derived from said UL42 sequence.

16. The method of claim 10 wherein said potential inhibitor comprises a UL42 fragment.

17. The method of claim 16 wherein said fragment is derived from the amino terminal half of said UL42 molecule.

18. A method of assaying a potential inhibitor for the ability to inhibit HSV infection, said method comprising the steps of
(1) providing HSV and cells capable of being infected with HSV,
(2) introducing into said cells separately or together DNA encoding a potential inhibitor of HSV replication and part or all of the HSV genome, wherein said inhibitor comprises an HSV DNA polymerase fragment or a fragment of UL42, and
(3) determining whether said inhibitor inhibits HSV production by said cells.

* * * * *

UNITED STATES PATENT AND TRADEMARK OFFICE
CERTIFICATE OF CORRECTION

PATENT NO. : 5,223,391
DATED : June 29, 1993
INVENTOR(S) : Donald M. Coen et al

It is certified that error appears in the above-indentified patent and that said Letters Patent is hereby corrected as shown below:

Column 3, line 38, "1(a) 1(c)" should be --1(a)-1(c)--.

Column 3, line 47, "pSP64 T" should be --pSP64-T--.

Column 4, line 15, insert --.-- after "present".

Column 5, line 37-38, "50 82 ]" should be --50 µl--.

Signed and Sealed this

Sixth Day of September, 1994

Attest:

BRUCE LEHMAN

*Attesting Officer*  *Commissioner of Patents and Trademarks*